United States Patent [19]
de Boer et al.

[11] Patent Number: 5,869,050
[45] Date of Patent: *Feb. 9, 1999

[54] METHODS OF BLOCKING T-CELL ACTIVATION USING ANTI-B7 MONOCLONAL ANTIBODIES

[75] Inventors: Mark de Boer, Almere, Netherlands; Leah B. Conroy, Pacifica, Calif.

[73] Assignee: Chiron Corporation, Emeryville, Calif.

[ * ] Notice: The term of this patent shall not extend beyond the expiration date of Pat. No. 5,425,797.

[21] Appl. No.: 15,147

[22] Filed: Feb. 9, 1993

Related U.S. Application Data

[63] Continuation-in-part of Ser. No. 910,222, Jul. 9, 1992, Pat. No. 5,397,703.
[51] Int. Cl.$^6$ .................. A61K 39/395; C07K 16/00
[52] U.S. Cl. ...................... 424/156.1; 424/137.1; 424/141.1; 424/133.1; 530/388.85; 530/387.1; 530/388.1; 530/387.5
[58] Field of Search ........................... 530/388.73, 389.6, 530/388.23, 387.1, 388.85, 387.5, 388.1; 424/85.8, 144.1, 133.1, 134.1, 156.1, 137.1, 141.1

[56] References Cited

U.S. PATENT DOCUMENTS

| | | | |
|---|---|---|---|
| 4,683,195 | 7/1987 | Mullis et al. . | |
| 4,683,202 | 7/1987 | Mullis . | |
| 4,689,299 | 8/1987 | Insel et al. . | |
| 4,816,567 | 3/1989 | Cabilly et al. . | |
| 4,886,796 | 12/1989 | Eichner et al. . | |
| 4,923,872 | 5/1990 | Kostlan et al. . | |
| 4,946,778 | 8/1990 | Ladner et al. | 435/69.6 |
| 5,068,223 | 11/1991 | Lipsky et al. . | |
| 5,100,899 | 3/1992 | Calne | 514/291 |
| 5,308,847 | 5/1994 | Calne | 514/262 |
| 5,330,993 | 7/1994 | Armistead et al. | 514/330 |
| 5,434,131 | 7/1995 | Linsley et al. | 514/2 |

FOREIGN PATENT DOCUMENTS

| | | |
|---|---|---|
| 9200092 | 1/1992 | WIPO . |
| WO 96/14865 | 5/1996 | WIPO . |

OTHER PUBLICATIONS

Kuplec–Weglinski et al., Synergistic interactions between anti–interleukin 2 receptor mab and CyA in snesitized rat recipients of cardiac allografts, Trans. Proc, vol. 23(1) pp. 285–286,1991.
Tufveson et al., New immunosupressants: testing and development in animals models and the clinic:with special reference to DSG. Immunol. Rev. vol. 136, pp. 110–109, 1993.
Cosimi, et al., "Use of Monoclonal Antibodies To T–Cell Subsets for Immunologic Monitoring and Treatment in Recipients of Renal Allografts", The New England Journal of Medicine, 305:308–313 (Aug. 6, 1981).
1992 Physician's Desk Reference at pp. 1217–1218, 1447–1448, 2024–2027 and 2332–2333.
Freeman, et al., "B7, A New Member Of The Ig Superfamily With Unique Expression On Activated And Neoplastic B Cells," 143:2714–2722 (Oct. 15, 1989).
Kriegler, et al., "A Novel Form Of TNF/Cachectin Is A Cell Surface Cytotoxic Transmembrane Protein: Ramifications For The Complex Physiology Of TNF," Cell 53:45–53 (Apr. 8, 1988).
Aruffo, et al., Molecular cloning of a CD28 cDNA by high–efficiency COS cell expression System, Proc. Natl. Acad. Sci. (USA), 84:8573–8577 (Dec., 1987).
Aruffo et al., The Lymphocyte Glycoprotein CD6 Contains a Repeated Domain Structure Characteristic of a New Family of Cell Surface and Secreted Proteins, J.Exp. Med., 174:949–952 (Oct., 1991).
Barneveld, et al., Monoclonal Antibodies against Human β–Glucocerebrosidase, Eur. J. Biochem., 134:585–589 (1983).
Boussiotis, et al., Activated human B lymphocyte express three CTLA–4 counterreceptors that costimulate T–Cell activation, Proc. Natl. Acad. Sci. (USA), 90:11059–11063 (Dec., 1993).
Cafiso, et al., Preparation of Unilamellar Lipid Vesicles at 37° C. by Vaporization Methods, Biochem. Biophys. Acta, 649:129–132 (1981).
de Boer, et al., Functional characterization of a novel anti–B7 monoclonal antibody, Eur. J. Immunol., 22:3071–3075 (1992).
de Boer, et al., Generation of monoclonal antibodies to human lymphocyte cell surface antigens using insect cells expressing recombinant proteins, J. Immunol. Methods, 152:15–23 (1992).
Dharakul, et al., Immunization with Baculovirus–Expressed Recombinant Rotavirus Proteins VP1, VP4, VP6, and VP7 Induces CD8$^+$ T Lymphocytes that Mediate Clearance of Chronic Rotavirus Infection in SCID Mice, J. Virol., 65(11:5928–5932 (Nov., 1991).
DiSanto, et al., Generation of anti–human CD8β–specific antibodies using transfectants expressing mixed–species CD8 heterodimers, J. Immunol. Methods, 141:123–131 (1991).
Fleming et al., In situ Expression of a B7–Like Adhesion Molecule on Keratinocytes from Human Epidermis, J. Investigative Dermatology, 101(5):754–758 (Nov., 1993).
Fraser, et al., Regulation of Interleukin–2 Gene Enhancer Activity by the T Cell Accessory Molecule CD28, Science, 251:313–316 (Jan. 18, 1991).
Freedman, et al., Selective Induction of B7/BB–1 on Interferon–γ Stimulated Monocytes: A Potential Mechanism for Amplification of T Cell Activation through the CD28 Pathway, Cell Immunol. 137:429–437 (1991).

(List continued on next page.)

*Primary Examiner*—Susan A. Loring
*Attorney, Agent, or Firm*—Donald J. Pochopien; Paul B. Savereide; Robert P. Blackburn

[57] ABSTRACT

Methods for causing T cell anergy, treating allograft transplant rejection, treating graft versus host disease, and preventing or treating rheumatoid arthritis are presented, the methods comprising co-administration of a molecule that binds to the B7 antigen and an immunosuppressive agent.

28 Claims, 11 Drawing Sheets

OTHER PUBLICATIONS

Gabizon, et al., Liposomes as In Vivo Carriers of Adriamycin: Reduced Cardiac Uptake and Preserved Antitumor Activity in Mice, Cancer Research, 42:4734–4739 (Nov., 1982).

Gimmi, et al., B–cell surface antigen B7 provides a costimulatory signal that induces T cells to proliferate and secrete interleukin 2, Proc. Natl. Acad. Sci. (USA), 88:6575–6579 (Aug., 1991).

Go et al., Anergized T Cell Clones Retain Their Cytolytic Ability, J. Immunol, 150(2):367–376 (Jan. 15, 1993).

Golub, Immunology A Synthesis, pp. 19–20, Sinauer Associates, Inc. (1987).

Haffar, et al., Costimulation of T–Cell activation and virus production by B7 antigen on activated $CD4^+$ T cells from human immunodeficiency virus type 1–infected donors, Proc. Natl. Acad. Sci. USA 90:11094–11098 (Dec., 1993).

Harding, et al., CD28–mediated signaling co–stimulates murine T cells and prevents induction of anergy in T–cell clones, Nature, 356:607–609 (Apr. 16, 1992).

Harper, et al., CTLA–4 and CD28 Activated Lymphocyte Molecules are Closely Related in Both Mouse and Human as to Sequence, Message Expression, Gene Structure, and Chromosomal Location, J. Immunol. 147(3):1037–1044 (Aug. 1, 1991).

Hathcock, et al., Identification of an Alternative CTLA–4 Ligand Costimulatory for T Cell Activation, Science, 262:905–911 (Nov. 5, 1993).

Hawrylowicz, et al., Regulation of Antigen–Presentation–I, IFN–γ Induces Antigen–Presenting Properties on B Cells, J. Immunol., 141(12)4083–4088 (Dec. 15, 1988).

Jenkins, et al., Antigen Presentation by Chemically Modified Splenocytes Induces Antigen–Specific T Cell Unresponsiveness in Vitro and in Vivo, J. Exp. Med. 165:302–319 (Feb., 1987).

Jenkins, et al., Allogenic Non–T Spleen Cells Restore the Responsiveness of Normal T Cell Clones Stimulated with Antigen and Chemically Modified Antigen–Presenting Cells, J. Immunol., 140(10)3324–3330 (May 15, 1988).

Jenkins, et al., Molecular events in the induction of a nonresponsive state in interleukin 2–producing helper T–lymphocyte clones, Proc. Natl. Acad. Sci. (USA), 84:5409–5413 (Aug., 1987).

June, et al., Evidence for the Involvement of Three Distinct Signals in the Induction of IL–2 Gene Expression in Human T Lymphocytes, J. Immunol., 143(1):153–161 (Jul. 1, 1989).

June et al., T–Cell Proliferation Involving the CD28 Pathway is Associated with Cyclosporine–Resistant Interleukin 2 Gene Expression, Mol. & Cell. Biol. 7(12):4472–4481 (Dec., 1987).

Knauf, et al., Relationship of Effective Molecular Size to Systemic Clearance in Rats of Recombinant Interleukin–2 Chemically Modified with Water–soluble Polymers, J. Bio. Chem., 263(29):15064–15070 (Oct. 15, 1988).

Kohler, et al., Continuous cultures of fused cells secreting antibody of predefined specificity, Nature, 256:495–497 (Aug. 7, 1975).

Kosco–Vilbois, et al., Follicular Dendritic Cells Help Resting B Cells to Become Effective Antigen–presenting Cells: Induction of B7/BB1 And Upregulation of Major Histocompatibility Complex Class II Molecules, J. Exp. Med. 178:2055–2066 (Dec., 1993).

Kubota, et al., Identification and Gene Cloning of a New Phosphatidylinositol–Linked Antigen Expressed on Mature Lymphocytes, J. Immunol., 145(11):3924–3931 (Dec. 1, 1990).

Lenschow, et al., Expression and functional significance of an additional ligand for CTLA–4, Prol. Natl. Acad., Sci. USA, 90:11054–11058 (1993).

Lin, et al., Long–Term Acceptance of Major Histocompatibility Complex Mismatched Cardiac Allografts Induced by CTLA4Ig Plus Donor–Specific Transfusion, J. Exp. Med., 178:1801–1806 (Nov., 1993).

Mueller, et al., Clonal Expansion Versus Functional Clonal Inactivation: A Costimulatory Signalling Pathway Determines the Outcome of T Cell Antigen Receptor Occupancy, Ann Rev. Immunol., 7:445–480 (1989).

Otten et al., Split Anergy in a CD8+ Cell: Receptor–Dependant Cytolysis in the Absence of Interleukin–2 Production, Science, 251:1228–1231 (Mar. 8, 1991).

Poznansky, Biological Approaches to the Controlled Delivery of Drugs: A Critical Review, Pharm. Revs. 36(4):277–336 (1984).

Ra, et al., A macrophage Fcγ receptor and the mast cell receptor for IgE share an identical subunit, Nature, 341:752–754 (Oct. 26, 1989).

Razi–Wolf, et al., Evidence for an additional ligand distinct from B7, for the CTLA–4 receptor, Proc. Natl. Acad. Sci. , USA 90:11182–11186 (Dec., 1993).

Schwartz, A Cell Culture Model for T Lymphocyte Clonal Anergy, Science, 248:1349–1356 (Jun. 15, 1990).

Schwartz, Costimulation of T Lymphocytes: The Role of CD28, CTLA–4, and B&/BB1 in Interleukin–2 Production and Immunotherapy, Cell, 71:1065–1068 (Dec. 24, 1992).

Sekine, et al., Expression of human papillomavirus type 6b E2 gene product with DNA–binding activity in insect (*Bombyx mori*) cells using a baculovirus expression vector, Gene, 65:187–193 (1988).

Selvakumar et al., Genomic organization and chromosomal location of the human gene encoding the B–lymphocyte activation antigen B7, Immunogenet., 36:175–181 (1992).

Smith, et al., Modification and secretion of human interleukin 2 produced in insect cells by a baculovirus expression vector, Proc. Natl. Acad. Sci. (USA), 82:8404–8408 (Dec., 1985).

Springer, et al., The Lymphocyte Function–Associated LFA–1, CD2, and LFA–3 Molecules: Cell Adhesion Receptors of the Immune System, Annu. Rev. Immunol., 5:223–252 (1987).

Springer, Adhesion receptors of the immune system, Nature, 346:425–434 (Aug. 2, 1990).

Szoka, Comparative Properties and methods of Preparation of Lipid Vesicles (Liposomes), Ann. Rev. Biophys. Bioeng., 9:467–508 (1980).

Takehara et al., Co–expression of the Hepatitis B Surface and Core Antigens Using Baculovirus Multiple Expression Vectors, J. Gen. Virol., 69:2763–2777 (1988).

Tan, et al., Induction of Alloantigen–specific Hyporesponsiveness in Human T Lymphocytes by Blocking Interaction of CD28 with its Natural Ligand B7/BB1, J. Exp. Med., 177:165–173 (Jan., 1993).

Thompson, et al., CD28 activation pathway regulates the production of multiple T–cell–derived lymphokine/cytokines, Proc. Natl. Acad. Sci. (USA), 86:1333–1337 (Feb., 1989).

Urakawa, et al., Synthesis of Immunogenic, but Non–infectious, Poliovirus Particles in Insect Cells by a Baculovirus Expression Vector, J. Gen. Virol. 70:1453–1463 (1989).

van Seventer et al., Roles of multiple accessory molecules in T–cell activation, Current Opinion in Immunology, 3:294–303 (1991).

Van Gool, et al., CD28 Litigation by Monoclonal Antibodies or B7/BB1 Provides an Accessory Signal for the Cyclosporin A–Resistant Generation of Cytotoxic T Cell Activity, J. Immunol., 150(8):3254–3263 (Apr. 15, 1993).

Vandenberghe, et al., Antibody and B7/BB1–mediated Ligation of the CD28 Receptor Induces Tyrosine Phosphorylation in Human T Cells, J. Exp. Med., 175:951–960 (Apr., 1992).

Vandenberghe, et al., In situ expression of B7/BB1 on antigen–presenting cells and activated B cells: an immunohistochemical study, Int. Immunol., 5(3):317–321 (1993).

Verweij, et al., Activation of Interleukin–2 Gene Transcription via the T–cell Surface Molecule CD28 is Mediated through an NF–kB–like Response element, J. Biol. Chem., 266(22):14179–14182 (Aug. 5, 1991).

Warmerdam, et al., A Single Amino Acid in the Second Ig–Like Domain of Human Fcγ Receptor II is Critical for Human IgG2 Binding, J. Immunol., 147(4):1338–1343 (Aug. 15, 1991).

Warmerdam, et al., Molecular Basis for a Polymorphism of Human Fcγ Receptor II (CD32), J. Exp. Med., 172:19–25 (Jul., 1990).

Weaver, et al., The costimulatory function of antigen–presenting cells, Immunol. Today, 11(2):49–55 (1990).

Webb et al., Cell–surface expression and purification of human CD4 produced in baculovirus–infected insect cells, Proc. Natl. Acad. Sci. (USA), 86:7731–7735 (Oct., 1989).

Young, et al., The B7/BB1 Antigen Provides One of Several Costimulatory Signals for the Activation of CD4+ T Lymphocytes by Human Blood Dendritic Cells In Vitro, J. Clin. Invest., 90:229–237 (Jul., 1992).

Brostoff, et al., Clinical Immunology, pub Gower Medical pp. 27.8 and 28.4–28.5 (1991).

Clark, et al., Association Between IL–6 and CD40 Signaling IL–6 Induces Phosphorylation of CD40 Receptors, J. Immunol., 145(5):1400–1406 (Sep. 1, 1990).

Co, et al., Humanized antibodies for therapy, Nature, 351:501–502, (Jun. 6, 1991).

Elliot, et al., Treatment of Rheumatoid Arthritis with Chimeric Monoclonal Antibodies to Tumor Necrosis Factor α, Arthritis & Rheumatism 36(12):1681–1690 (Dec., 1993).

Freeman, et al., Cloning of B7–2: A CTLA–4 Counter–Receptor That Costimulates Human T Cell Proliferation, Science, 262:909–911 (Nov. 5, 1993).

Harris, et al., Therapeutic antibodies—the coming of age, Tibtech, 11:42–44, (Feb. 1993).

Mondino, et al., Surface proteins involved in T cell costimulation, Journal of Leukocyte Biology, 55:805–815 (Jun., 1994).

Sato, et al., Biological Effects in Vitro of Monoclonal Antibodies ot Human Epidermal Growth Factor Receptors, Mol. Biol. Med., 1:511–529 (1983).

Webb, Arthritis wonder cure wins cautious welcome, Science, p. 16, (Feb. 12, 1994).

Winter, et al., Antibody–based Therapy, Humanized antibodies, TIPS, 14:139–143, (May, 1993).

Freeman, et al., Uncovering of Functional Alternative CTLA–4 Counter–Receptor in B7 Deficient Mice, Science, 262:907–909 (Nov. 5, 1993).

van Gool, et al., Synergy Between Cyclosporin A and Monoclonal Antibody to B7 in Blocking Alloantigen–Induced T–Cell Activation, Blood, 83(1):176–183 (Jan. 1, 1994).

Yokochi, et al.; Journal of Immunology, vol. 128, pp. 823–827; 1982.

Freedman, et al.; Journal of Immunology, vol. 139, pp. 3260–3267; 1987.

Valle, et al.; Immunology, vol. 69, pp. 531–535; 1990.

Linsley, et al.; Science, vol. 257, pp. 792–795; Aug. 7, 1992.

Lenschow, et al.; Science, vol. 257, pp. 789–792; Aug. 7, 1992.

June, et al.; Immunology Today, vol. 11, No. 6, pp. 211–216; 1990.

Linsley, et al.; Journal of Experimental Medicine, vol. 174, pp. 561–569; Sep. 1991.

Beidler, et al., "Cloning and High Level Expression of a Chimeric Antibody With Specificity For Human Carcinoembryonic Antigen," J. Immunol., 141: 4053–4060 (1988).

Better, et al., "*Escherichia coli* Secretion of an Active Chimeric Antibody Fragment," Science, 240: 1041–1043 (1988).

Boulianne, et al., "Production of Functional Chimaeric Mouse/Human Antibody," Nature, 312: 643–646 (1984).

Jones, et al., "Replacing The Complementarity–determining Regions In A Human Antibody With Those From A Mouse," Nature, 321: 522–525 (1986).

Liu, et al., "Production Of A Mouse–Human Chimeric Monoclonal Antibody To CD20 with Potent Fc–Dependent Biologic Activity," J. Immunol., 139: 3521–3526 (1987).

Morrison, "Transfectomas Provide Novel Chimeric Antibodies," Science, 229: 1202–1207 (1985).

Neuberger, et al., "A Hapten–specific Chimaeric IgE Antibody With Human Physiological Effector Function," Nature, 314: 268–270 (Mar., 1985).

Oi, et al. "Chimeric Antibodies," BioTechniques, 4(3): 214–221 (1986).

Reichmann, et al., "Reshaping Human Antibodies For Therapy," Nature, 332: 323–327 (1988).

Rodwell, "Engineering Monoclonal Antibodies," Nature, 342: 99–100 (1989).

Verhoeyen, et al., "Reshaping Human Antibodies: Grafting an Antilysozyme Activity," Science, 239: 1534–1536 (1988).

Full length B7:

Forward MR67 5'-GCG CTGCAG CATCTGAAGCCATGGGCC-3' (307-324)

Backward MR68 5'-CGC GGTACC TTGCTTCTGCGGACACTG-3' (1182-1199)

Soluble B7:

Forward MR67 5'-GCG CTGCAG CATCTGAAGCCATGGGCC-3' (307-324)

Backward MR145 5'-GCGC GGTACC TTACTCCATGGGCATGTATTCCTCTTCCTGTTATCAGGAAAATGCTGTTG-3' (1022-1042)

Full length CD40:

Forward MR108 5'-GCGT AGATCT GGTCTCACCTGCCATGGTTCG-3' (34-55)

Backward MR112 5'-GCGT GGTACC CCACACTCCTGGGTGGGTGCAGCC-3' (882-905)

Soluble CD40:

Forward MR108 5'-GCGT AGATCT GGTCTCACCTGCCATGGTTCG-3' (34-55)

Backward MR150 5'-GCGT GGTACC TTACTCCATGGGCATGTATTCCTCTTCCTCATCAGTCTTGTTGTGCCTGC-3' (575-596)

FIG. 2

METHODS OF BLOCKING T-CELL ACTIVATION USING ANTI-B7 MONOCLONAL ANTIBODIES

CROSS-REFERENCE TO RELATED APPLICATIONS

This application is a continuation-in-part of U.S. application Ser. No. 07/910,222, filed Jul. 9, 1992, now U.S. Pat. No. 5,397,703, the disclosure of which is hereby incorporated by reference.

FIELD OF THE INVENTION

This invention relates to novel methods of treating diseases of the immune system. In particular, this invention relates to methods of preventing or treating transplant rejection, graft versus host disease, and other immunological conditions arising from the recognition of specific antigens as foreign.

BACKGROUND OF THE INVENTION

Current strategies for the prevention of graft rejection after transplantation are based on the use of broad acting immunosuppressive agents such as cyclosporin A (CsA), FK506 and corticosteroids. These drugs must often be taken over long periods of time and therefore increase the risk of serious infections, nephrotoxicity, and cancer. In addition, not all patients can tolerate high doses of these immunosuppressive agents, often resulting in graft rejection or graft-versus-host disease (GVHD). Optimal prevention of graft rejection should be based on the induction of specific tolerance to the donor tissue. Thus, the ideal drug for prevention of transplant rejection should induce clonal unresponsiveness, or anergy, of donor-reactive T cells, without the need for long-term immunosuppression. Anergy is thought to be the result of intercellular signaling after interaction between the T-cell receptor (TCR) and the peptide-presenting major histocompatibility complex (MHC) antigen in the absence of a "costimulatory" signal. Mueller, D. L. et al., *Annu. Rev. Immunol.* (1989) 7:445. This costimulatory signal is normally provided by the cell surface of antigen-presenting cells (APCs). Hawrylowicz, C. M. et al., *J. Immunol.* (1988) 141:4083; and Springer, T. A. et al., *Annu. Rev. Immunol.* (1987) 5:223.

T Cell Activation

T cells play an important role during the normal in vivo immune response. They are involved in cytotoxicity, delayed type hypersensitivity, and T cell-dependent antibody production by B cells. Furthermore, T cells can produce a wide variety of lymphokines such as interleukin-2 (IL-2), tumor necrosis factor alpha (TNF-α), lymphotoxin, gamma interferon (IFN-γ), and granulocyte macrophage colony stimulating factor (GM-CSF).

The activation of T cells is the result of ligand-receptor interactions. Under physiological conditions, the TCR/CD3 complex binds to antigenic peptides presented by the MHC molecules of APCs. The TCR/CD3 complex plays two roles in antigen-induced activation. First, it recognizes a specific antigen in the context of an antigen-presenting MHC molecule. Then, the recognition event is transmitted through the plasma membrane by a signalling mechanism. However, binding of antigen to the TCR alone is not sufficient for maximum T cell activation. A number of other accessory molecules on the surface of the T cell are known to play important roles in adhesion or signalling or both. For instance, the CD2 molecule on T cells can bind to LFA-3 on APCs, but it has also been shown that binding of antibodies to CD2 can augment the signals provided by the TCR/CD3 complex. Other ligand pairs involved in T cell activation are LFA-1/ICAM-1, CD4/MHC-class II antigen, VLA-4/VCAM, and, most importantly, CD28/B7.

The CD28 and B7 Antigens

The likely candidate for the costimulatory signal that determines whether TCR-stimulation leads to full T cell activation or to T cell anergy is that generated by interaction of CD28 on the T cells with B7 on APCs. It has been demonstrated in vitro that cross-linking of the CD28 molecule can rescue T cells from becoming anergic. Harding, F. A. et al., *Nature* (1992) 356:607. CD28 is a homodimeric transmembrane glycoprotein with an apparent molecular mass of 44 kDa and is a member of the immunoglobulin superfamily (Aruffo, A. & Seed, B. *PNAS* (*USA*) (1987) 84:8573). The CD28 molecule is expressed on approximately 95% of CD4-positive T cells and 50% of CD8-positive T cells. Costimulation of T cells with monoclonal antibody to the TCR/CD3 complex and CD28 results in greatly enhanced T cell activation. Thompson, C. B. et al., *PNAS* (*USA*) (1989) 86:1333–1337; June, C. H. et al., *J. Immunol.* (1989) 143:153–161; and Lindsten, T. et al., *Science* (1989) 244:339–343. This effect apparently involves stabilization of mRNA for several lymphokines, including IL-2, resulting in a greatly enhanced production of these lymphokines. June, C. H. et al., supra; and Lindsten, T. et. al., supra. Furthermore, a CD28-responsive element has been demonstrated in the enhancer of the IL-2 gene, suggesting that there is also regulation at the transcriptional level. Fraser, J. D. et al., *Science* (1991) 251:313 and Verwey, C. L. et al., *J. Biol. Chem.* (1991) 266:14179–14182. Certain models of T cell activation mediated by CD28 have been reported to be relatively resistant to inhibition with CsA. June, C. H. et al., *Mol. Cell. Biol.* (1987) 7:4472–4481.

B7 is a monomeric transmembrane glycoprotein with an apparent molecular mass of 45–65 kDa and is, like CD28, a member of the immunoglobulin superfamily. Freeman, G. J. et al., *J. Immunol.* (1989) 143:2714–2722. Moreover, B7-expressing CHO cells are able to synergize with TCR stimulation, resulting in IL-2 secretion and T cell proliferation. Linsley, P. S. et al., *J. Exp. Med.* (1991) 137:721–730; and Gimmi, C. D. et al., *PNAS* (*USA*) (1991) 88:6575. B7 also binds to a recombinant fusion protein of the CTLA-4 molecule. Linsley, P. S. et al., *J. Exp. Med.* (1991) 174:561–569. CTLA-4, too, is a member of the immunoglobulin superfamily, and the cytoplasmic regions of CTLA-4 and CD28 show significant homology. Harper, K. et al., *J. Immunol.* (1991) 147:1037. The B7 molecule is expressed on activated B cells (Freeman, G. J. et al., supra), monocytes stimulated with IFN-γ (Freedman, A. S. et al., *Cell. Immunol.* (1991) 137:429–437), and isolated peripheral blood dendritic cells (Young, J. W. et al., *J. Clin. Invest.* (1992) 90:229–237). Immunohistochemical studies have shown that the B7 molecule is also constitutively expressed in vivo on dendritic cells in both lymphoid and non-lymphoid tissue. Vandenberghe, P. et al., "International Immunology" (1993).

In vivo, the B7 antigen is involved in T cell activation during transplant rejection. Lenschow and co-workers have used a soluble fusion protein of human CTLA-4 and the immunoglobulin G1 Fc region (CTLA4Ig), which strongly binds to both mouse and human B7, to prevent rejection of human pancreatic islets after transplantation in mice (Lenschow, D. J. et al., *Science* (1992) 257:789–792). Here CTLA4Ig blocks rejection of a xenoantigen (an antigen foreign to the species from which the T cell is derived).

Molecules that interfere with the interaction between the B7 and CD28 antigens are known in the art. The soluble CTLA4-Ig fusion protein is known to partially block this interaction. Linsley, P. S. et al., *J. Exp. Med.* (1991) 74:561. Anti-CD28 antibodies are also known to block this interaction. Furthermore, anti-B7 antibodies are known in the art. Yokochi, T. et al., *J. Immunol.* (1982) 128:823; Freedman, A. S. et al. *J. Immunol.* (1987) 139:3260; Valle, A. et al. *Immunol* (1990) 69:531. Commonly owned, co-pending U.S. application Ser. No. 07/910,222 describes the generation of one such monoclonal antibody (mAb) called B7-24.

However, nothing in the art relates to (1) the use of anti-B7 antibodies to cause T cell anergy and thereby prevent or treat graft rejection or GVHD, or (2) the use of molecules that bind to the B7 antigen in conjunction with other immunosuppressive agents to cause T cell anergy and thereby prevent or treat graft rejection or GVHD.

SUMMARY OF THE INVENTION

The current invention is based on the discovery that the coadministration of a molecule that binds to the B7 antigen and an immunosuppressive agent to a patient can induce long-lasting T cell anergy against an alloantigen (an antigen native to the same species as the T cell).

Accordingly, it is a primary object of this invention to provide a method for preventing transplant rejection in a patient, the method comprising administering to a patient in need of such treatment therapeutically effective amounts of (1) a molecule that binds to the B7 antigen and (2) an immunosuppressive agent such as cyclosporin A, FK506, or a corticosteroid, in a pharmaceutically acceptable excipient. In a preferred embodiment of this invention, the molecule that binds to the B7 antigen is an anti-B7 antibody.

It is a further object of this invention to provide a method for preventing or treating graft versus host disease (GVHD) in a patient, the method comprising administering to a patient in need of such treatment therapeutically effective amounts of (1) a molecule that binds to the B7 antigen and (2) an immunosuppressive agent such as cyclosporin A, FK506, or a corticosteroid, in a pharmaceutically acceptable excipient. In a preferred embodiment of this invention, the molecule that binds to the B7 antigen is an anti-B7 antibody.

It is another object of this invention to provide a method for preventing or treating rheumatoid arthritis in a patient, the method comprising administering to a patient in need of such treatment therapeutically effective amounts of (1) a molecule that binds to the B7 antigen and (2) an immunosuppressive agent such as cyclosporin A, FK506, or a corticosteroid, in a pharmaceutically acceptable excipient. In a preferred embodiment of this invention, the molecule that binds to the B7 antigen is an anti-B7 antibody.

In more preferred embodiments of the above methods, the anti-B7 antibody is a monoclonal antibody, most preferably B7-24.

BRIEF DESCRIPTION OF THE DRAWINGS

FIG. 4A shows the results of staining ARC EBV transformed cells with serum from a mouse immunized with B7 expressing Sf9 cells (solid line) or with normal mouse serum (dotted line). FIG. 4B shows the results of staining ARC EBV transformed cells with serum from a mouse immunized with CD40 expressing Sf9 cells (solid line) or with normal mouse serum (dotted line). FIG. 4C shows the results of staining ARC EBV transformed cells with serum from a mouse immunized with control Sf9 cells (solid line) or with normal mouse serum (dotted line).

DETAILED DESCRIPTION OF THE INVENTION

Figure 1:
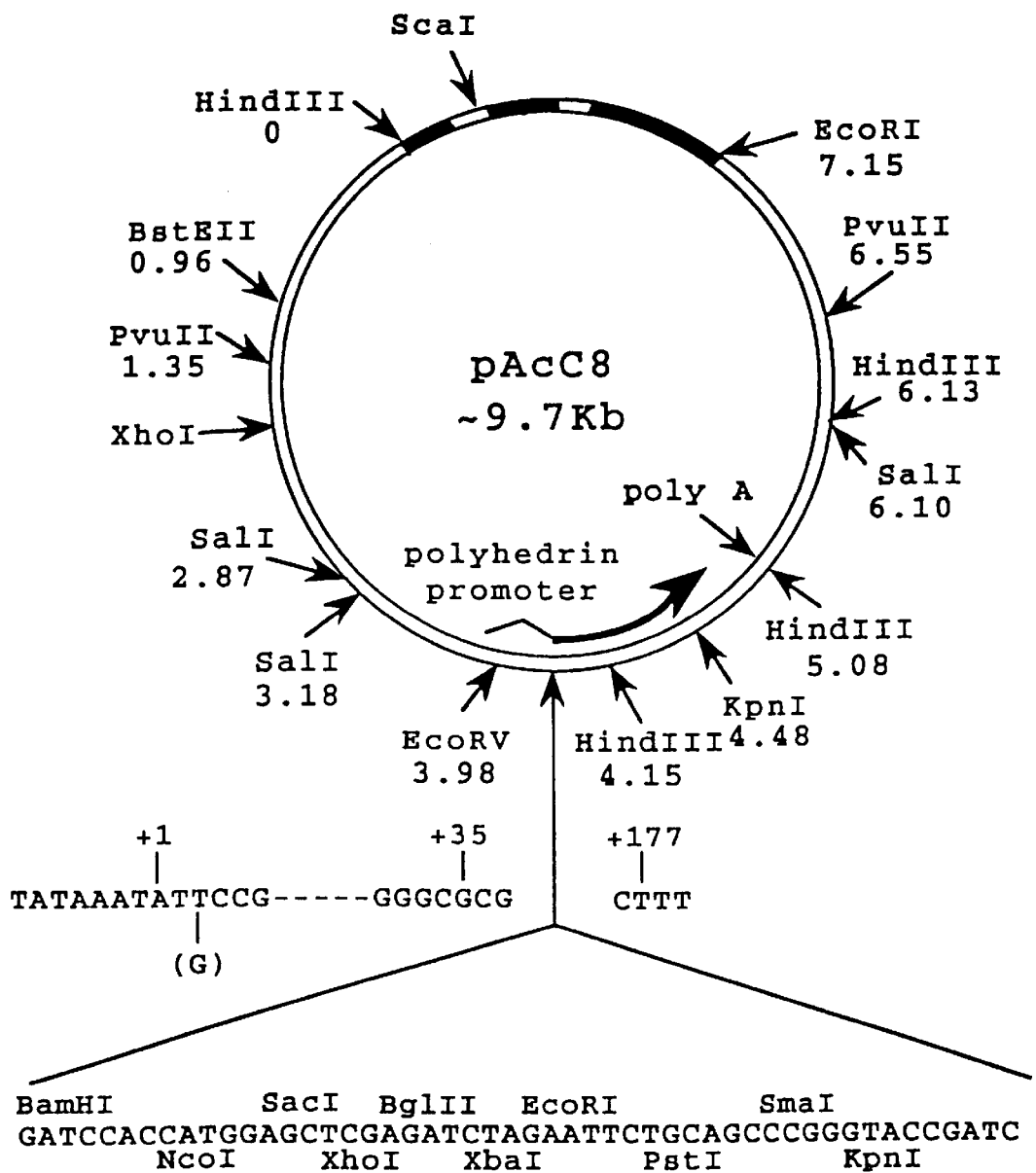
FIGS. 1A and 1B show a schematic representation of the baculoviral transfer vector pAcC8 and the sequence of the multiple cloning site (1A) and a schematic representation of the generation of Sf9 cells which express human CD40 or B7 antigen (1B).

The invention described herein draws on previously published work and pending patent applications. By way of example, such work consists of scientific papers, patents or pending patent applications. All of these publications and applications, cited previously or below are hereby incorporated by reference.

Definitions

As used herein, the term "molecule which binds to the B7 antigen" means a molecule which is capable of forming a complex with the B7 antigen in an environment wherein other substances in the same environment are not complexed to the B7 antigen. The complex is formed in a manner that blocks the normal signal transduction pathway of B7 through the CD28 or CTLA4 antigen. Molecules which bind to the B7 antigen include CD28, CTLA4, CTLA4Ig and anti-B7 antibodies.

As used herein, the term "antibody" refers to polyclonal antibodies, monoclonal antibodies, humanized antibodies, single-chain antibodies, and fragments thereof such as $F_{ab}$, $F_{(ab')2}$, $F_v$, and other fragments which retain the antigen binding function of the parent antibody.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as $F_{ab}$, $F_{(ab')2}$, $F_v$, and others which retain the antigen binding function of the antibody. Monoclonal antibodies of any mammalian species can be used in this invention. In practice, however, the antibodies will typically be of rat or murine origin because of the availability of rat or murine cell lines for use in making the required hybrid cell lines or hybridomas to produce monoclonal antibodies.

As used herein, the term "humanized antibodies" means that at least a portion of the framework regions of an immunoglobulin are derived from human immunoglobulin sequences.

As used herein, the term "single chain antibodies" refer to antibodies prepared by determining the binding domains (both heavy and light chains) of a binding antibody, and supplying a linking moiety which permits preservation of the binding function. This forms, in essence, a radically abbreviated antibody, having only that part of the variable domain necessary for binding to the antigen. Determination and construction of single chain antibodies are described in U.S. Pat. No. 4,946,778 to Ladner et al.

The Composition

The composition of the current invention comprises two components which together are therapeutically effective in preventing or treating graft rejection, GVHD, or rheumatoid arthritis. The two components are: (1) a molecule that binds to the B7 antigen such as MAb B7-24; and (2) an immunosuppressive agent.

Molecules that bind to the B7 antigen include CD28, CTLA4, CTLA4Ig and anti-B7 antibodies.

1. Antibody Preparation

Monoclonal antibody B7-24 is prepared as described in Example 1 herein. Other monoclonal antibodies of the invention may be prepared similarly, or as follows. First, polyclonal antibodies are raised against the B7 antigen. Second, monoclonal antibodies specific for B7 are selected.

a. Polyclonal Sera

Polyclonal sera may be prepared by conventional methods. In general, a solution containing the B7 antigen is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the antigen-containing solution in saline, preferably in an adjuvant such as Freund's complete adjuvant, and injecting the mixture or emulsion parenterally (generally subcutaneously or intramuscularly). A dose of 50–200 µg/injection is typically sufficient. Immunization is generally boosted 2–6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization.

Polyclonal antisera are obtained by bleeding the immunized animal into a glass or plastic container, incubating the blood at 25° C. for one hour, followed by incubating at 4° C. for 2–18 hours. The serum is recovered by centrifugation (e.g., 1,000×g for 10 minutes). About 20–50 ml per bleed may be obtained from rabbits.

b. Monoclonal Antibodies

Monoclonal antibodies are prepared using the method of Kohler and Milstein, *Nature* (1975) 256:495–96, or a modification thereof. Typically, a mouse or rat is immunized as described above. However, rather than bleeding the animal to extract serum, the spleen (and optionally several large lymph nodes) are removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the desired immunizing cell-surface antigen (and which do not bind to unrelated antigens). The selected MAb-secreting hybridomas are then cultured either in vitro (e.g., in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}I$, or with an anti-biotin MAb labeled with HRP. Other permutations and possibilities will be readily apparent to those of ordinary skill in the art, and are considered as equivalents within the scope of the instant invention.

2. Immunosuppressive Agents

The antibodies of the invention are given in combination with one or more immunosuppressive agents. Immunosuppressive agents are agents that block or inhibit the activation or proliferation of T cells. The immunosuppressive agents according to this invention include cyclosporin A (CsA), corticosteroids (methotrexate, prednisolone, dexamethasone), FK506, and rapamycin. Preferably the immunosuppressive agent is cyclosporin A, FK506 or a corticosteroid, most preferably cyclosporin A.

Formulations and Methods of Administration

The compositions of this invention are administered at a concentration that is therapeutically effective to halt transplant rejection, or prevent GVHD or rheumatoid arthritis. To accomplish this goal, the compositions may be formulated using a variety of acceptable excipients known in the art. Typically, the compositions are administered by injection, either intravenously or intraperitoneally. Methods to accomplish this administration are known to those of ordinary skill in the art. It may also be possible to obtain compositions which may be topically or orally administered, or which may be capable of transmission across mucous membranes.

Before administration to patients, formulants may be added to the antibodies. A liquid formulation is preferred. For example, these formulants may include oils, polymers, vitamins, carbohydrates, amino acids, salts, buffers, albumin, surfactants, or bulking agents. Preferably carbohydrates include sugar or sugar alcohols such as mono, di, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. Sucrose is most preferred. "Sugar alcohol" is defined as a $C_4$ to $C_8$ hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v % and 7.0 w/v %, more preferable between 2.0 and 6.0 w/v %. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Most any physiological buffer may be used, but citrate, phosphate, succinate, and glutamate buffers or mixtures thereof are preferred. Most preferred is a citrate buffer. Preferably, the concentration is from 0.01 to 0.3 molar. Surfactants that can be added to the formulation are shown in EP Nos. 270,799 and 268,110.

Additionally, antibodies can be chemically modified by covalent conjugation to a polymer to increase its circulating half-life, for example. Preferred polymers, and methods to attach them to peptides, are shown in U.S. Pat. Nos. 4,766,106; 4,179,337; 4,495,285; and 4,609,546 which are all hereby incorporated by reference in their entireties. Preferred polymers are polyoxyethylated polyols and polyethylene glycol (PEG). PEG is soluble in water at room temperature and has the general formula: R(O—$CH_2$—$CH_2$)$_n$O—R where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it win be understood that the type and amount of the reactive groups may be varied to achieve a covalently conjugated PEG/antibody of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, *J. Bio. Chem.* 263:15064–15070, and a discussion of POG/IL-2 conjugates is found in U.S. Pat. No. 4,766,106, both of which are hereby incorporated by reference in their entireties.

Another drug delivery system for increasing circulatory half-life is the liposome. Methods of preparing liposome delivery systems are discussed in A. Gabizon et al., *Cancer Research* (1982) 42:4734; D. S. Cafiso, *Biochem Biophys Acta* (1981) 649:129; F. Szoka, *Ann Rev Biophys Eng* (1980) 9:467. Other drug delivery systems are known in the art and are described in, e.g., M. J. Poznansky et al., DRUG DELIVERY SYSTEMS (R. L. Juliano, ed., Oxford, N.Y. 1980), pp. 253–315; M. L. Poznansky, *Pharm Revs* (1984) 36:277.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

As stated above, the antibodies and compositions of this invention are used to treat human patients to prevent or treat transplant rejection, GVHD or rheumatoid arthritis. The preferred route of administration is parenterally. In parenteral administration, the compositions of this invention will be formulated in a unit dosage injectable form such as a solution, suspension or emulsion, in association with a pharmaceutically acceptable parenteral vehicle. Such vehicles are inherently nontoxic and nontherapeutic. Examples of such vehicles are saline, Ringer's solution, dextrose solution, and Hanks' solution. Nonaqueous vehicles such as fixed oils and ethyl oleate may also be used. A preferred vehicle is 5% dextrose in saline. The vehicle may contain minor amounts of additives such as substances that enhance isotonicity and chemical stability, including buffers and preservatives.

The dosage and mode of administration will depend on the individual. Generally, the compositions are administered so that antibodies are given at a dose between 1 $\mu$g/kg and 20 mg/kg, more preferably between 20 $\mu$g/kg and 10 mg/kg, most preferably between 1 and 7 mg/kg. Preferably, it is given as a bolus dose, to increase circulating levels by 10–20 fold and for 4–6 hours after the bolus dose. Continuous infusion may also be used after the bolus dose. If so, the antibodies may be infused at a dose between 5 and 20 $\mu$g/kg/minute, more preferably between 7 and 15 $\mu$g/kg/minute.

The present invention will now be illustrated by reference to the following examples which set forth particularly advantageous embodiments. However, it should be noted that these embodiments are illustrative and are not to be construed as restricting the invention in any way.

EXAMPLES

Materials and Methods

Cells and Cell Lines. Peripheral blood mononuclear cells were isolated from heparinized blood (obtained from healthy volunteers) by Ficoll-Hypaque density centrifugation. T cells were enriched by depleting monocytes and B cells using Lymphokwik (Lambda, Calif.) (1 λ). The EBV-transformed B cell line ARC and the P815 cell line, a NK-resistant murine mastocytoma cell line that expresses FcγRII and FcγRIII (Ra, C. et al., *Nature* (1989) 341:752), were obtained from the ATCC (Rockville, Md.). 3T6-FcγRII, the mouse fibroblast cell line expressing CD32, the human FcγRII high responder allele, as described by Warmerdam, P. A. M. et al.,*J. Exp. Med.* (1990) 172:19, was kindly provided by Dr. J. van de Winkel (University Hospital, Utrecht, The Netherlands).

Culture Media. Purified T cells and EBV-transformed B cells were cultured in Iscove's modification of Dulbecco's modified Eagle's medium supplemented with streptomycin (200 U/ml), and 10% heat-inactivated fetal bovine serum (complete IMDM). 3T6-FcγRII cells were cultured in medium consisting of 50% Dulbecco's modified Eagle's medium and 50% HAM-F10 medium, supplemented with aminopterin (0.2 μg./ml), thymidine (5 μg/ml), xanthine (10 μg/ml), hypoxanthine (15 μg/ml), mycophenolic acid (20 μg/ml) deoxycytidine (2.3 μg/ml), and 10% heat-inactivated fetal bovine serum (complete DME/HAM-F10). 3T6-FcγRII/B7 cells were cultured in complete DME/HAM-F10 medium containing 400 μg/ml G418 (Gibco).

Monoclonal Antibodies. Mab B7-24 (IgG2a, χ) was obtained from a fusion with splenocytes from a mouse immunized with Sf9 insect cells expressing the human B7 molecule (de Boer, M. et al., *J. Immunol. Methods.* (1992) 152:15–23) as described in commonly-owned copending U.S. application Ser. No. 07/910,222, and was used as purified antibody. Purified anti-B7 Mab BB-1, as described by Yokochi, T. et al., *J. Immunol.* (1982) 128:823–827, was used as purified antibody and was a gift of Dr. E. A. Clark (University of Washington, Seattle, Wash.). Anti-CD3 Mab CLB-T3/4.1 (IgG1, χ) was used as diluted tissue culture supernatant and was kindly supplied by Dr. L. Aarden (Central Laboratory of the Red Cross Blood Transfusion Service, Amsterdam, The Netherlands). Anti-CD3 Mab UCHT1 (IgG, χ) was used as purified antibody and as a gift of Dr. P. Beverley (Imperial Research Cancer Fund, London, UK). Anti-CD72 Mab WL225 (IgG2a, χ) was used as purified antibody and was a gift of Dr. K. Thielemans (Vrije Universiteit Brussel, Belgium). The anti-ICAM-1 Mab 84H10 was used as diluted ascites fluid.

Fluorescent Cell Staining (FACS) Assay. Cells ($10^6$/sample) were incubated in 10 μl primary antibody (10 μl/ml in PBS-BSA or HBSS (Hanks' Balanced Salt Solution, Gibco/BRL) supplemented with 1% BSA and 0.05% sodium azide) for 20 minutes at 4° C. After 3 washes with PBS-BSA or HBSS-BSA, the cells were incubated in 100 μl FITC-labeled $F_{ab'2}$ fragments of goat anti-(mouse IgG) antibodies (Jackson, West Grove, Pa.) for 20 minutes at 4° C. After 3 washes with PBS-BSA or HBSS-BSA and 1 wash with PBS, the cells were resuspended in 0.5 ml PBS. Analyses were performed with a FACSSCAN V (Becton Dickinson, San Jose, Calif.).

B7-Mediated T Cell Proliferation Assay. Purified T cells were cultured with 3T6 fibroblasts transfected with the FcγRIIa high responder allele and the B7 molecule (de Boer, M. et al., *Eur. J. Immunol.* (1992) 22:3071–3075). Proliferation was measured by $^3$H-thymidine incorporation. Briefly, $4\times10^4$ T cells were cultured with $10^4$ irradiated (2500 rads) 3T6-FcγRII/B7 cells in 96-well flat-bottom tissue culture plates in 200 μl/well complete IMDM with or without anti-CD3 Mab CLB-T3/4.1. During the last 16 hours of a 72 hour culture period, the cells were pulsed with 1 μCi/well $^3$H-thymidine. Proliferation of T cells is expressed as the mean cpm of triplicate wells.

Cytotoxic T Cell Assay. Purified T cells were cultured with 3T6 fibroblasts transfected with the FcγRIIa high responder allele and the B7 molecule. Briefly, $10^6$ T cells were cultured with $0.2\times10^6$ irradiated (2500 rads) 3T6-FcγRII/B7 cells in 24-well flat-bottom tissue culture plates in 1 ml/well complete IMDM in the presence of anti-CD3 Mab UCHT1 for 3–4 days. The cytotoxic activity of the lymphocytes was analyzed in an anti-CD3-redirected cytotoxicity assay as described below.

Mixed Lymphocyte Culture Assay. Proliferation of purified T cells was measured in mixed lymphocyte cultures (MLC) using the EBV-transformed B cell line ARC as stimulator cells. $5\times10^4$ T cells were cultured with $5\times10^4$ irradiated (5000 rads) stimulator cells in 96-well round-bottom tissue culture plates (Corning) in 200 μl/well complete IMDM medium. During the last 16 hours of a 72 hour culture period, the cells were pulsed with 1 μCi/well $^3$H-thymidine. Proliferation of T cells is expressed as the mean cpm of triplicate wells. For secondary MLCs, cells were stimulated as described above for primary MLC. The T cell blasts for secondary MLC were generated in 5- to 7-day primary MLC, with subsequent culture in the absence of the stimulator cells for 2–4 days. The cytotoxic activity of T cells generated in primary or secondary MLC was analyzed in an anti-CD3-redirected cytotoxicity assay using the mouse P815 cells as described below. Alternatively, the EBV-transformed B cells used to induce the CTL activity served as target cells.

Cytotoxicity Assay. CTL activity was determined in a 4 hour target cell lysis assay using P815 murine mastocytoma cells or ARC EBV-transformed B cells as targets. In the case of the P815 target cells the CTLs were bridged non-specifically to the target cells using the anti-CD3 Mab OKT3 at 2 μg/ml. When the ARC cells were used as target cells, only the alloantigen-specific CTLs participate in the killing process. $10^6$ target cells were incubated with 200 μCi of $^{51}$Cr-sodium chromate (Amsersham International) for one hour and subsequently washed. The CTL assays were performed in 96-well V-bottom microtiter plates using 5000 $^{51}$Cr-labelled target cells with different amounts of effector cells in a total volume of 200 μl/well. Four wells were filled with $5\times10^3$ target cells in 200 μl medium alone, and four wells with $5\times10^3$ target cells in 100 μl medium and 100 μl saponin (for evaluation of spontaneous and maximal release, respectively). In the case of the P815 cells, three wells were filled with effector cells and target cells in the absence of anti-CD3 Mab (to determine the background experimental lysis). Three other wells also contained the anti-CD3 Mab at 2 μg/ml in order to determine the total lysis in the presence of anti-CD3. The plates were centrifuged for 10 minutes at 200×g and incubated for four hours at 37° C. Afterwards, 100 μl of the supernatant of each well was counted in a gamma counter. Results are expressed as percentage of anti-CD3-dependent specific release with the P815 target cells, or as a percentage of alloantigen-specific release with the ARC target cells.

Example 1

Making Monoclonal Antibodies to B7 and CD40
A. PCR Cloning of CD40 and B7

RNA was isolated from a population of EBV-transformed human spleen cells essentially as described by Chirgwin et al., *Biochemistry* (1979) 17:5294. In brief, the cells were washed twice with phosphate buffered saline (PBS) and lysed in 5M guanidinium thiocyanate in the presence of 0.7M 2-mercaptoethanol. The cell lysate was layered on a discontinuous CsCl gradient (Chirgwin et al.) and centrifuged for 16 hours at 26,000 rpm in a Beckman SW28 rotor. The RNA was recovered by dissolving the pellet in DEPC-treated H$_2$O. The RNA was precipitated with ethanol once, resuspended in DEPC-treated H$_2$O, and stored at −70° C.

Figure 2:
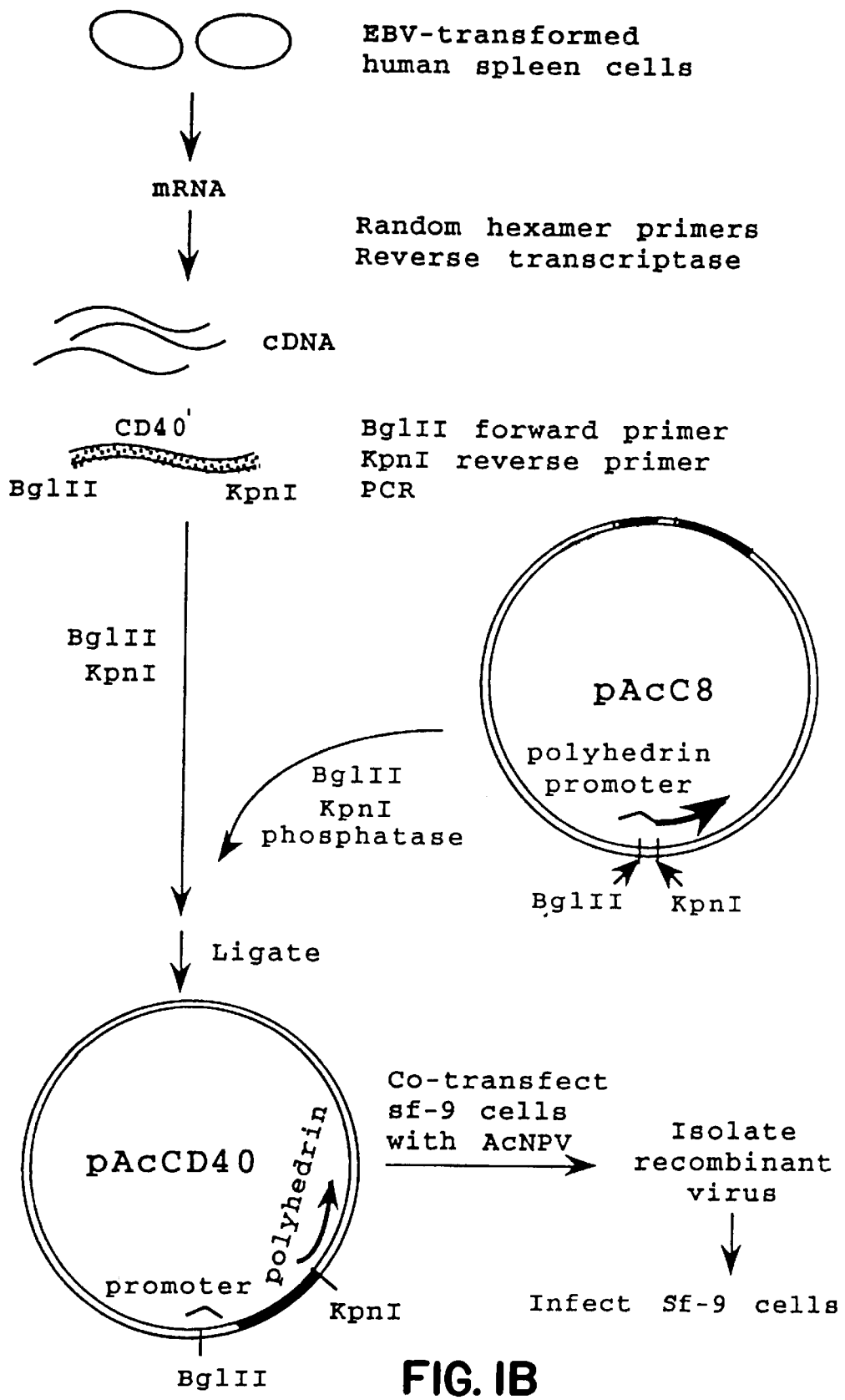
FIG. 2 shows the sequences of polymerase chain reaction primers used in the preparation of coding regions for human CD40 and human B7 antigens. These primers were constructed on the basis of the published complete DNA coding sequences for antigens B7 and CD40.

Total RNA (10 μg/reaction) was converted to cDNA using random hexamer priming in 50 μl reaction buffer containing 500 units MLV-RT (Bethesda Research Laboratories, Bethesda, Md.), 5 μM random hexamer (Pharmacia, Piscataway, N.J.), 1 mM DTT, dNTP mix (0.5 mM each), 10 mM Tris-HCL pH 8.3, 50 mM KCl, 2.5 mM MgCl$_2$ and 0.1 mg/ml BSA (bovine serum albumin). After incubation at 37° C. for 1 hour, the samples were boiled for 3 minutes and stored at −70° C. The DNA encoding the CD40 and B7 molecules was generated by PCR using primers which contained sequences having homology to known CD40 and B7 sequence, where the primers also encoded restriction sites useful for cloning (FIG. 2). These primers were based on the published cDNA coding sequences for B7 and CD40 (Freeman et al., *J. Immunol.* (1989) 143:2714, Stamenkovic et al., *EMBO J.* (1989) 8:1403). All primers start with a C-G clamp at the 5' end followed by a restriction site for cloning (shown in bold, FIG. 2). The underlined sequences in the backward primers, for the cloning of the soluble forms of B7 and CD40, represents an epitope recognized by a monoclonal antibody used for affinity purification. The numbers in brackets represent the location of the primers relative to the published cDNAs for CD40 and B7.

For PCR amplification, 1 μl of cDNA was mixed with 1 μl (10 picomoles) of a forward primer, 1 μl (10 picomoles) of a backward primer, and 47 μl of PCR mix. The PCR mix consisted of 1.25 units Taq polymerase (Perlin-Elmer/Cetus, Norwalk, Conn.), dNTP mix (0.2 mM each), 10 mM Tris-cHL pH 8.3, 50 mM KCl, 2.5 mM MgCl$_2$ and 0.1 mg/ml BSA. The 50 μl of PCR mixture was overlaid with 70 μl mineral oil and subjected to 25 cycles of amplification in a Perlin-Elmer/Cetus thermocycler (denaturation at 95° C. for 30 seconds, primer annealing at 55° C. for 30 seconds and extension at 72° C. for 1.5 minutes). PCR products were obtained after 25 amplification cycles.

The amplification products were digested with BglII and KpnI (FIG. 1B) and isolated by size-fractionation. Before expression in baculovirus, the DNA sequence of each fragment was confirmed by sequencing analysis to prevent the introduction of PCR-induced mutations. The baculovirus transfer vector pAcC8 was also digested with BglII and KpnI (FIG. 1B).

The amplified fragments were ligated to the linear pAcC8 vector (ratio of insert to vector was 3:1). The ligation products were transformed into bacterial strain DH5α (Gibco/BRL, Gaithersburg Md.) and recombinant pAcC8 vectors were selected on the basis of ampicillin resistance. Recombinant plasmids were isolated from bacterial clones (Maniatis et al.; Ausubel et al.) and the presence of the insert of interest verified using polymerase chain reactions (see above). Large scale plasmid preparation was performed by standard procedures (Ausubel et al.; Maniatis et al; Sambrook et al.)

B. Baculovirus Expression of Human CD40 and B7

Sequences encoding human CD40 and human B7 were recombined into the *Autographa californica* baculovirus (AcNPV) using the transfer vectors pAcCD40 (encoding the full-length CD40 molecule), pAcCD40-ED/Glu (encoding the extracellular domain of CD40), pAcB7 (encoding the full-length B7 molecule) and pCcB7-ED/Glu (encoding the cellular domain of the B7 molecule).

The plasmids were cotransfected with wild-type baculoviral DNA (2–10 pfu) (AcNPV; Summers et al.) into Sf9 (*Spodoptera frugiperda*) cells at a density of 10$^6$ cells/ml (Summers et al.). Recombinant baculovirus-infected Sf9 cells were identified and clonally purified (Summers et al.).

For cell surface expression of recombinant proteins the cells were harvested after 48 hours of culture; for the production of secreted recombinant proteins, the cells were harvested after 72 hours of culture.

C. Sf9 Insect Cell ELISA

Sf9 insect cells infected with recombinant virus were cultured for 48 hours in 24-well plates. After removal of the tissue culture medium the plates were incubated for 45 minutes at room temperature (RT) with 0.25 ml of antibody in PBS with 1% BSA (PBS-BSA). After three washed with PBS-BSA, the plates were incubated for 35 minutes at RT with 250 μl of a 1/250 dilution of goat anti-(mouse total Ig) immunoglobulins conjugated to horseradish peroxidase (Zymed, South San Francisco, Calif.) in PBS-BSA. Unbound peroxidase activity was removed by washing five times with PBS-BSA. Bound peroxidase activity was revealed by the addition of an assay mixture prepared by diluting 0.5 ml of 2 mg/ml 3,3',5,5'-tetramethylbenzidine in ethanol to 10 ml with 10 mM sodium acetate, 10 mM EDTA buffer (pH 5.0) and adding 0.03% (v/v) H$_2$O$_2$. The reaction was stopped after 10 minutes by adding 100 μl of 1M H$_2$SO$_4$.

Figure 3:
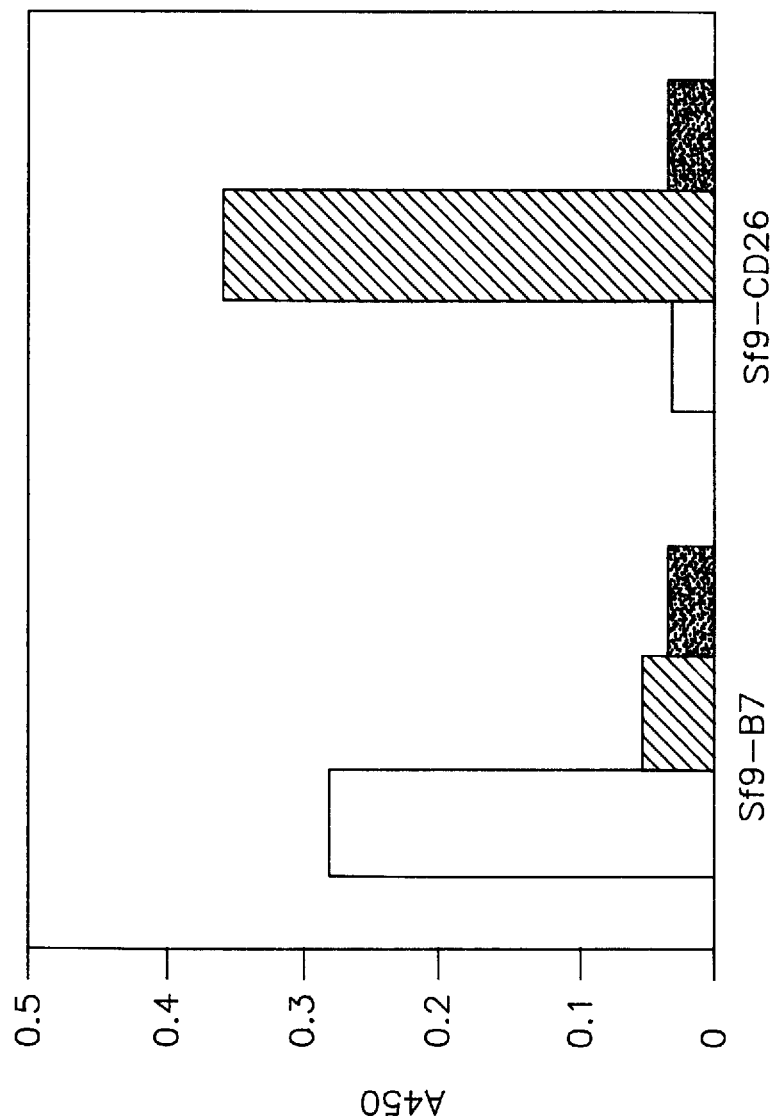
FIG. 3 shows the results of ELISA assays examining the reaction of anti-B7 monoclonal antibody BB-1 with Sf9 cells infected with AcB7 virus and with Sf9 cells expressing human CD26. The antibodies used in the ELISA assays were BB-1 (anti-B7, open bars), Ta-1 (anti-CD26, hatched bars) and no primary antibody (gray bars).

The above-described ELISA assays performed on live Sf9 cells gave the following results. FIG. 3 presents the data for Sf9 cells infected with pAcB7 and pAcCD26 which were cultured for 48 hours in 24-well plates. The antibodies used in the ELISA were: BB-1 (anti-B7, open bars), Ta-1, (anti-CD26, hatched bars) and no primary antibody (gray bars).

D. Host Animal Immunization

Female BALB/c mice were injected intraperitoneally at day 0 and day 14 with 5×10$^6$ Sf9 cells infected with AcCD40 virus, AcB7 virus or AcCd3 virus (control virus). At day 21, 100 μl of serum was obtained to test for the presence of specific antibodies. After a rest period of at least two weeks, the mice received a final injection with 5×10$^6$ cells infected with AcCD40 or AcB7 virus. Three days after this last injection, the spleen cells were used for cell fusion.

E. Generation of Hybridoma Clones

Splenocytes from immunized BALB/c mice were fused with SP2/0 murine myeloma cells at a ratio of 10:1 using 50% polyethylene glycol as previously described by de Boer et al. (1988). The fused cells were resuspended in complete IMDM medium supplemented with hypoxanthine (0.1 mM), aminopterin (0.01 mM), thymidine (0.016 mM) and 0.5 ng/ml hIL-6 (Genzyme, Cambridge, Mass.). The fused cells were then distributed between the wells of 96-well tissue culture plates, so that each well contained 1 growing hybrid on average.

Figure 4:
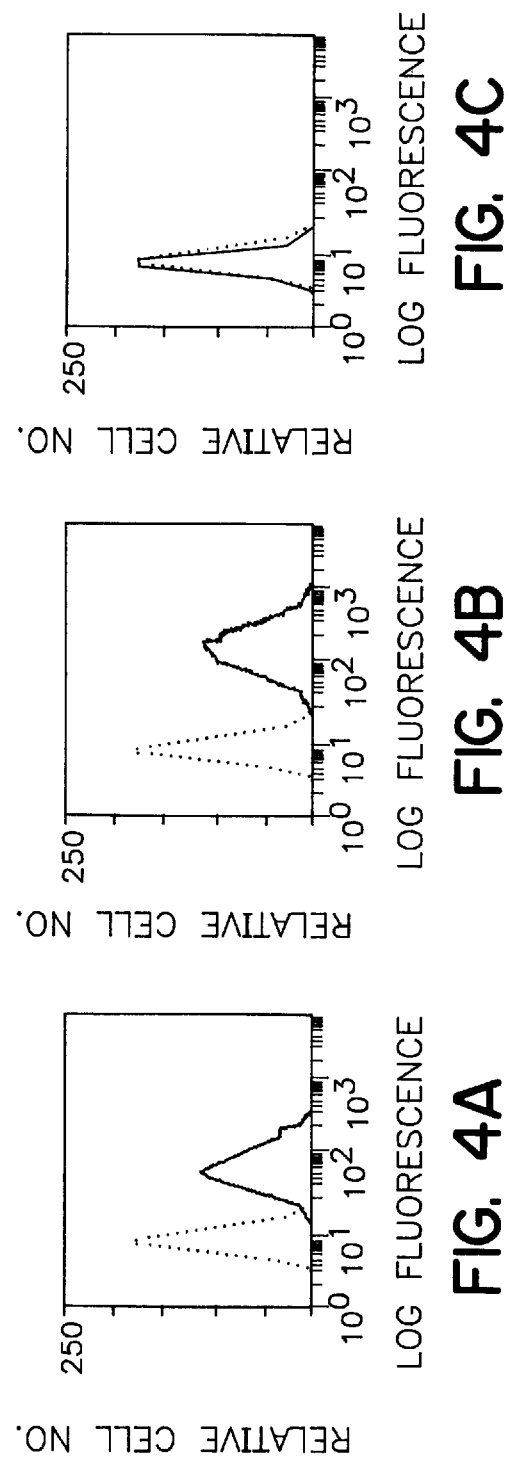
FIGS. 4A–4C show the results of the fluorescent cell staining of EBV-transformed B cell line ARC cells expressing B7.

After 10–14 days the supernatants of the hybridoma populations were screened for specific antibody production. For the screening of specific antibody production by the hybridoma clones, the supernatants of 12 wells were pooled and used for fluorescent cell staining of EBV-transformed B cells as described for the FACS Assay above. The data is presented in FIGS. 4A and 4B, which show the results for starting at 1:100 dilution of serum from mice immunized with B7-expressing Sf9 cells (solid line) or a 1:100 dilution of normal mouse serum (dotted line). FIG. 4C used serum from a mouse immunized with normal insect cells.

Subsequently, the supernatants of the positive pools were tested individually. Positive hybridoma cells were cloned three times by limiting dilution in IMDM/FBS containing 0.5 ng/ml hIL-6. One such hybridoma expressing an anti-B7 antibody was labelled B7-24.

Example 2

Blocking T Cell Proliferation with Mab B7-24

We studied the role of the B7 molecule in T cell activation using the proliferation and MLC assays described above.

Figure 5:
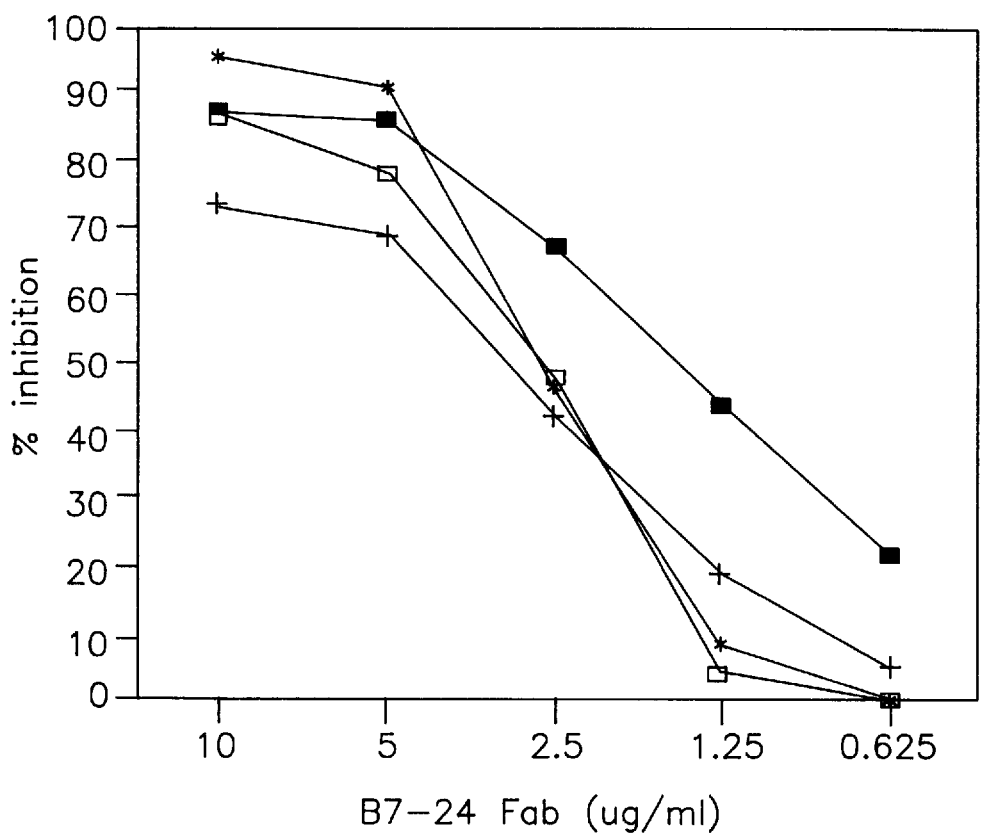
FIG. 5 shows the inhibition of anti-CD3-induced, B7-mediated proliferation of T cells by Fab fragments of anti-B7 Mab B7-24.

Proliferation in the absence of B7-24 Fab fragments ranged from 20,000 to 60,000 cpm. FIG. 5 shows that this Mab binds to a functionally important domain of the B7 molecule, since it can completely block anti-CD3-induced, B7-mediated induction of T cell proliferation. Data shown are the ±S.D. of 4 individual experiments using T cells of different donors.

Figure 6:
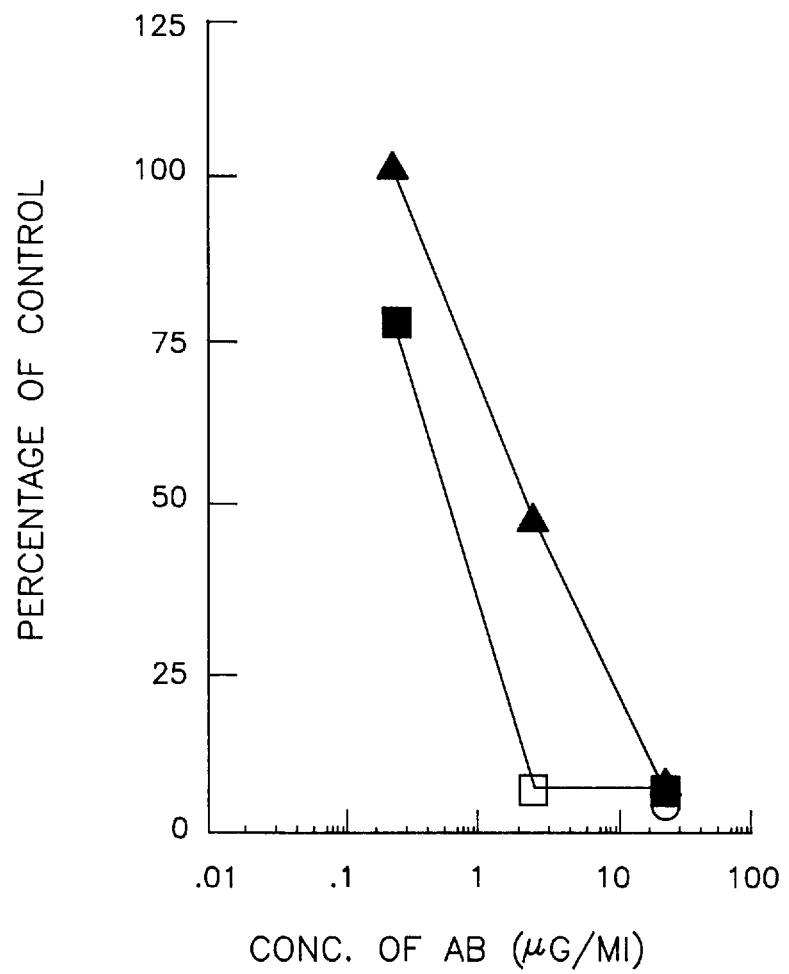
FIG. 6 shows the inhibition of anti-CD3-induced, B7-mediated proliferation of T cells by anti-B7 Mabs B7-24 (squares) or BB-1 (triangles).
Figure 7A:
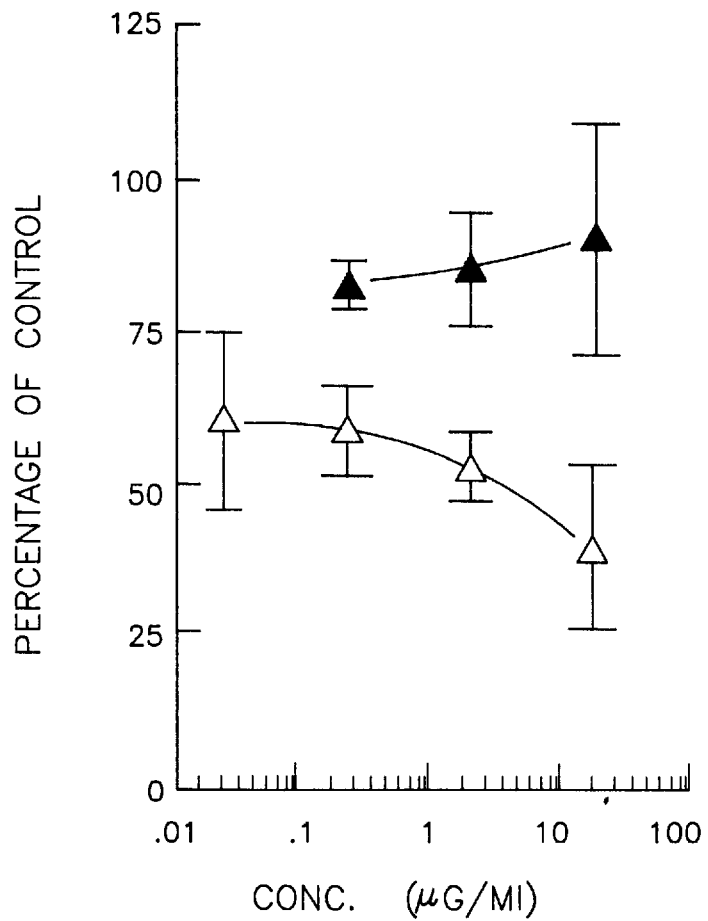
FIG. 7 shows the effect of blocking B7/CD28 interaction using (A) MAb B7-24 or (B) MAb BB-1 during 3-day primary MLC (closed symbols), and 3-day secondary MLC (open symbols).
Figure 7B:
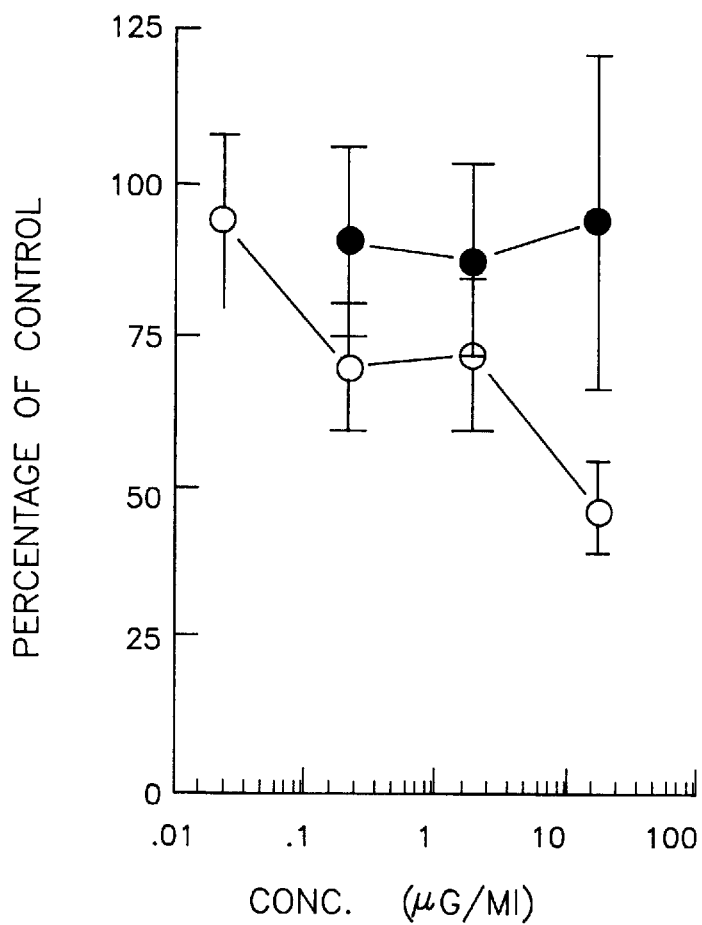

FIG. 6 shows the inhibition of anti-CD3-induced, B7-mediated proliferation of T cells by anti-B7 Mabs B7-24 (squares) or BB-1 (triangles). It was therefore surprising to find that Mab B7-24 could not inhibit T cell activation in primary MLC using B7-positive EBV-transformed B cells as stimulator cells. FIG. 7 shows the effect of blocking B7/CD28 interaction during primary MLC (closed symbols) and secondary MLC (open symbols). Purified T cells were stimulated with the EBV-transformed B cell line ARC for 3 days in the presence or absence of different concentrations of Mab B7-24 (FIG. 7A) or BB-1 (FIG. 7B). Proliferation in the absence of antibody ranged from 15,000 to 30,000 in primary MLC and from 20,000 to 60,000 in secondary MLC. Data shown are the mean ±S.D. of 4 individual experiments using T cells from different donors.

From this experiment, it is clear that anti-B7 monoclonal antibodies cannot completely block primary MLCs. Under the same experimental conditions, however, a Mab to CD3 could almost completely block the activation of T cells in the primary MLC. Interestingly, when Mab B7-24 was tested for its inhibitory capacity in secondary mixed lymphocyte cultures using pre-activated T cells, it was able to inhibit the activation of T cells.

Example 3

Blocking T Cell Proliferation with Cyclosporin A and/or Mab B7-24

Figure 8:
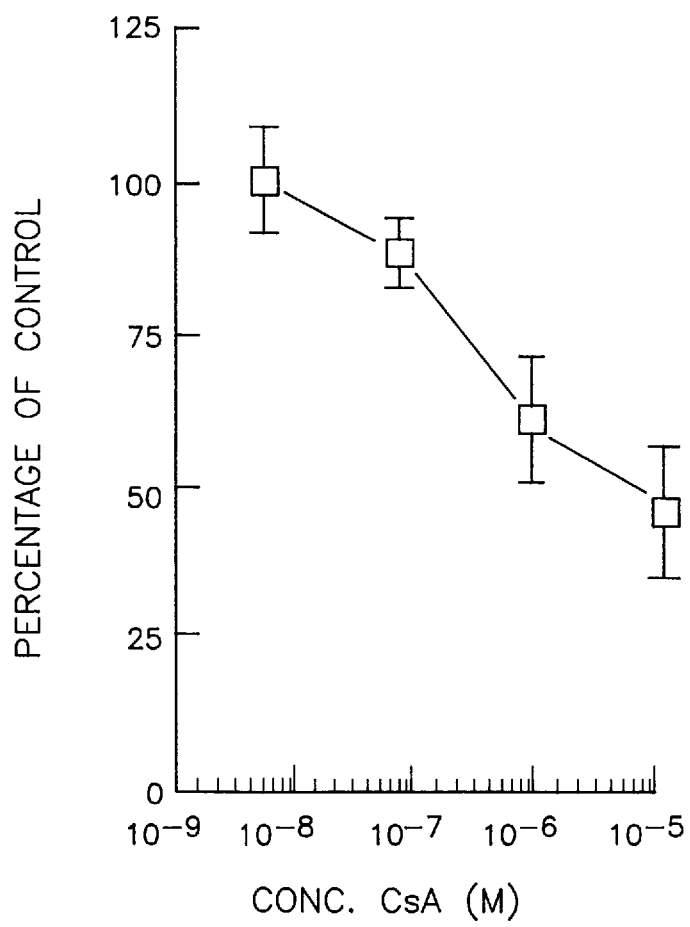
FIG. 8 shows the inhibition of anti-CD3-induced, B7-mediated proliferation of T cells by CsA. Data are the mean ±S.D. of 3 individual experiments using T cells of different donors.

We used the proliferation assay described above to determine whether the costimulation of T cells with B7 is also resistant to inhibition with CsA. FIG. 8 shows that when T cells are induced to proliferate with anti-CD3 Mab, costimulation with B7 can be inhibited in a dose-dependent manner by CsA. However, it was not possible to completely block the activation of T cells with CsA concentrations that are not toxic. When CsA was used to block primary MLC (results not shown) or secondary MLC (see Table 1), similar results were obtained. These experiments clearly suggest that B7-CD28/CTLA4 mediated T cell proliferation is only partially sensitive to the inhibitory action of CsA. This lack of complete inhibition when T cells are costimulated with B7 in vitro could mimic what happens in vivo during graft rejection or acute GVHD despite treatment with CsA.

Table 1 shows that CsA alone or mAb B7-24 alone gave a dose-dependent, but incomplete, inhibition of T cell activation. However, when CsA and B7-24 were combined, T cell activation was completely blocked. Interestingly, addition of 0.025 μg/ml B7-24 gave almost the same amount of blocking as 2.5 μg/ml. Furthermore, in the presence of 0.025 μg/ml B7-24, decreasing the CsA concentration 60-fold still resulted in more than 90% inhibition of T cell activation, being more than the maximal inhibition with the highest CsA concentration alone.

This synergy between Mab B7-24 and CsA was specific for the B7/CD28 interaction, since it was not observed using Mabs to either ICAM-1 or CD72 in the same proliferation assay, as shown in Table 2.

TABLE 2

Effects of CsA with B7, ICAM-1 or CD72 Mabs in blocking T-cell proliferation in a secondary MLC

| Monoclonal Antibody | Concentration (μg/ml) | Cyclosporin A Concentration | | | |
|---|---|---|---|---|---|
| | | $6 \times 10^{-7}$M | $3 \times 10^{-7}$M | $10^{-7}$M | None |
| B7-24 (α-B7) | 2.5 | 3 | 3 | 3 | 40 |
| | 0.25 | 3 | 2 | 3 | 33 |
| | 0.025 | 6 | 6 | 6 | 47 |
| 84H10 (α-ICAM-1) | 2.5 | 76 | 84 | 81 | 115 |
| | 0.25 | 80 | 80 | 76 | 99 |
| | 0.025 | 91 | 99 | 96 | 99 |
| WL225 (α-CD72) | 2.5 | 106 | 107 | 89 | 98 |
| | 0.25 | 108 | 106 | 91 | 100 |
| | 0.025 | 109 | 105 | 93 | 106 |

*Table entries reflect T-cell proliferation in CPM. Proliferation was measured using the T-cell proliferation assay described above.

Example 4

Blocking T Cell Proliferation with Mab B7-24 and Other Immunosuppressive Agents

The protocol of Example 3 above is used to show the blocking of T cell proliferation using Mab B7-24 in conjunction with other immunosuppressive agents. The proliferation assay protocol in Example 3 is followed substituting (A) FK506, (B) rapamycin, (C) methotrexate, (D) prednisolone, or (E) dexamethasone for CsA.

Example 5

Blocking Cytotoxic T Lymphocyte Activity with Cyclosporin A and/or Mab B7-24

We used the cytotoxicity assay described above to test whether CsA and B7-24 could also cooperate in blocking

TABLE 1

CsA and Mab B7-24 Synergy in blocking T-cell Proliferation in Secondary MLC*

| B7-24 (μg/ml) | Cyclosporin A concentration | | | | | | |
|---|---|---|---|---|---|---|---|
| | $6 \times 10^{-6}$M | $3 \times 10^{-6}$M | $10^{-6}$M | $6 \times 10^{-7}$M | $3 \times 10^{-7}$M | $10^{-7}$M | None |
| 2.5 | 971 | 609 | 601 | 790 | 697 | 1,159 | 25,209 |
| 0.25 | 553 | 545 | 601 | 788 | 559 | 882 | 20,753 |
| 0.025 | 897 | 939 | 1,121 | 1,592 | 1,570 | 2,818 | 29,364 |
| None | 12,687 | 15,593 | 23,484 | 24,589 | 27,629 | 33,235 | 62,598 |

Figure 9:
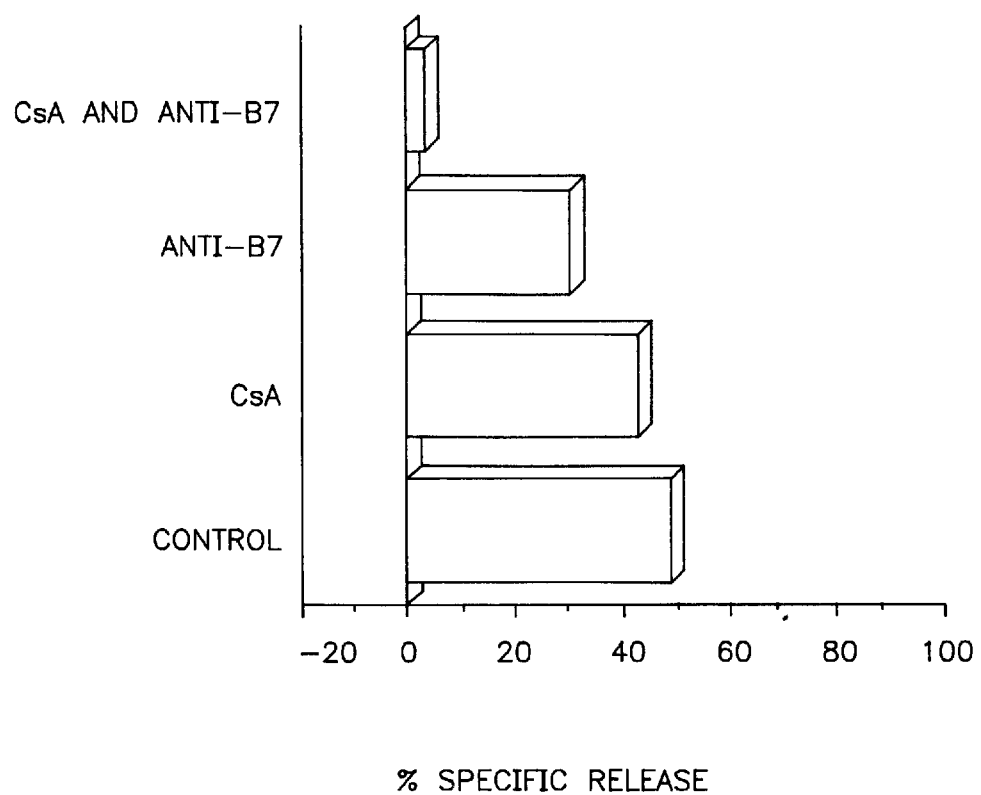
FIG. 9 shows the synergistic effects of anti-B7 Mab B7-24 and CsA in blocking allo-antigen-induced CTL activity during secondary MLC. CTL activity of the T cells was analyzed after restimulation for 3 days with the EBV-transformed B cell line ARC in the presence of medium alone; 400 $\mu$g/ml CsA; 10 $\mu$g/ml Mab B7-24; or 400 $\mu$g/ml CsA and 10 $\mu$g/ml Mab B7-24.

*Table entries reflect T-cell proliferation in CPM. Proliferation was measured using the T-cell proliferation assay described above. Data shown for one of four experiments.

induction of CTL activity in alloantigen-specific activation of T cells. Purified T cells were stimulated with the EBV-transformed B cell line ARC for 6 days, followed by a 2-day culture period in medium alone. CTL activity of the T cells was analyzed after restimulation for 3 days with the EBV-transformed B cell line ARC in the presence of medium alone; 400 μg/ml CsA; 10 μg/ml Mab B7-24; or 400 μg/ml CsA and 10 μg/ml Mab B7-24, as shown in FIG. 9. T cells activated by the alloantigen in these cultures were efficiently induced to become cytolytic, since about 50% of the ARC target cells could be lysed in the 4 hour assay. This induction of CTL activity in secondary MLC could only be slightly inhibited with 400 ng/ml CsA. Addition of 10 μg/ml Mab B7-24 during the secondary MLC resulted in about 40% inhibition. However, combining CsA and Mab B7-24 resulted in almost complete blockage of the CTL activation.

Example 6

Blocking Cytotoxic T Lymphocyte Activity with Mab B7-24 and Other Immunosuppressive Agents The protocol of Example 5 above is used to show the blocking of cytotoxic T lymphocyte activity using Mab B7-24 in conjunction with other immunosuppressive agents. The cytotoxicity assay protocol in Example 5 is followed substituting (A) FK506, (B) rapamycin, (C) methotrexate, (D) prednisolone, or (E) dexamethasone for CsA.

Example 7

Combining CsA and Mab B7-24 During Alloantigen-Specific T-Cell Activation

We investigated whether T cells stimulated in a primary MLC assay (as described above) with the alloantigen in the presence of CsA and Mab B7-24 could respond to secondary antigen stimulation. Purified T cells were stimulated with the EBV-transformed B cell line ARC for 6 days in the presence or absence of 10 μg/ml Mab B7-24 and 400 μg/ml CsA, followed by a 2 day culture period in medium alone. CTL activity of the T cells was analyzed after re-stimulation for 3 days with the EBV-transformed B cell line ARC. The data in Table 3 is that of a representative experiment, showing that 6-day exposure to the alloantigen in the presence of both CsA and Mab B7-24, but not in the presence of CsA or Mab B7-24 alone, resulted in total unresponsiveness for subsequent challenge with the alloantigen in secondary MLC. This unresponsiveness was not due to lack of viability of the cells after the primary MLC, since in a control experiment the cell population could still be induced to become cytotoxic after stimulation with immobilized anti-CD3 Mab or cells expressing a non-related alloantigen (results not shown).

TABLE 3

Alloantigen-Specific T Cell Tolerance Induced by the combination of CsA and B7-24.

| Additions of Culture Medium During Primary MLC* | (% specific release) | |
|---|---|---|
| | P815 | ARC |
| None | 80 | 49 |
| B7-24 (10 μg/ml) | 78 | 24 |
| CsA (400 ng/ml) | 76 | 37 |
| B7-24 & CsA | 0 | 0 |

*CTL activity of purified T cells in secondary MLC with ARC cells as stimulator cells, after primary MLC as described above. CTL activity measured in T cell cytotoxicity assay as described above.

Example 8

Combining Mab B7-24 and an Immunosuppressive Agent During Alloantigen-Specific T-Cell Activation The protocol of Example 7 above is used to show the ability of Mab B7-24 in conjunction with other immunosuppressive agents to block secondary antigen stimulation. The CTL assay protocol in Example 7 is followed substituting (A) FK506, (B) rapamycin, (C) methotrexate, (D) prednisolone, or (E) dexamethasone for CsA.

Deposition of Cultures

The hybridomas used in the above examples, to illustrate the method of the present invention were deposited in and accepted by the American Type Culture Collection (ATCC), 12301 Parklawn Drive, Rockville, Md., 20852 USA, under the terms of the Budapest Treaty.

| Culture | Deposit Date | Accession No. |
|---|---|---|
| B7-24-E1G4 | May 6, 1993 | HB11341 |

The deposited cell line, B7-24-E1G4, is identical to the B7-24 cell line described in the present application in terms of the antibody produced, the former being a subclone of the latter.

The deposited cell line, B7-24-E1G4, is identical to the B7-24 cell line described in the present application in terms of the antibody produced, the former being a subclone of the latter.

The present invention has been described with reference to specific embodiments. However, this application is intended to cover those changes and substitutions which may be made by those skilled in the art without departing from the spirit and the scope of the appended claims.

We claim:

1. A method for treating transplant rejection in a patient, the method comprising administering to a patient in need of such treatment a therapeutically effective amount of (a) a molecule that specifically binds to the B7 antigen, said molecule upon binding to the B7 antigen, blocking the normal signal transduction pathway of B7 through the CD28 or CTLA4 pathways, said molecule being an antibody or an antigen binding fragment thereof; and (b) an immunosuppressive agent in a pharmaceutically acceptable excipient.

2. The method of claim 1, wherein the molecule that binds to the B7 antigen is an anti-B7 antibody.

3. The method of claim 2, wherein the anti-B7 antibody is a monoclonal antibody.

4. The method of claim 2, wherein the anti-B7 antibody is a humanized antibody.

5. The method of claim 3, wherein the monoclonal antibody is mAb B7-24 which is secreted by a hybridoma having ATCC accession number HB 11341.

6. The method of claim 1, wherein the immunosuppressive agent is selected from the group consisting of cyclosporin A, FK506, rapamycin and a corticosteroid.

7. The method of claim 6, wherein the immunosuppressive agent is cyclosporin A.

8. A method for treating graft versus host disease in a patient, the method comprising administering to a patient in need of such treatment a therapeutically effective amount of (a) a molecule that specifically binds to the B7 antigen, said molecule upon binding to the B7 antigen, blocking the normal signal transduction pathway of B7 through the CD28 or CTLA4 pathways, said molecule being an antibody or an antigen binding fragment thereof; and (b) an immunosuppressive agent in a pharmaceutically acceptable excipient.

9. The method of claim 8, wherein the molecule that binds to the B7 antigen is an anti-B7 antibody.

10. The method of claim 9, wherein the anti-B7 antibody is a monoclonal antibody.

11. The method of claim 9, wherein the anti-B7 antibody is a humanized antibody.

12. The method of claim 10, wherein the monoclonal antibody is mAb B7-24 which is secreted by a hybridoma having ATCC accession number HB 11341.

13. The method of claim 8, wherein the immunosuppressive agent is selected from the group consisting of cyclosporin A, FK506, rapamycin and a corticosteroid.

14. The method of claim 13, wherein the immunosuppressive agent is cyclosporin A.

15. A method for treating rheumatoid arthritis in a patient, the method comprising administering to a patient in need of such treatment a therapeutically effective amount of (a) a molecule that specifically binds to the B7 antigen, said molecule upon binding to the B7 antigen, blocking the normal signal transduction pathway of B7 through the CD28 or CTLA4 pathways, said molecule being an antibody or an antigen binding fragment thereof; and (b) an immunosuppressive agent in a pharmaceutically acceptable excipient.

16. The method of claim 15, wherein the molecule that binds to the B7 antigen is an anti-B7 antibody.

17. The method of claim 16, wherein the anti-B7 antibody is a monoclonal antibody.

18. The method of claim 16, wherein the anti-B7 antibody is a humanized antibody.

19. The method of claim 17, wherein the monoclonal antibody is mAb B7-24 which is secreted by a hybridoma having ATCC accession number HB 11341.

20. The method of claim 15, wherein the immunosuppressive agent is selected from the group consisting of cyclosporin A, FK506 and a corticosteroid.

21. The method of claim 20, wherein the immunosuppressive agent is cyclosporin A.

22. The method of claim 21 wherein said antibody or fragment thereof is humanized.

23. A method for treating transplant rejection in a human patient, the method comprising administering to a human patient in need of such treatment a therapeutically effective amount of (a) an anti-B7 monoclonal antibody or an antigen binding fragment thereof, said antibody or fragment thereof binding to a B7 antigen on an antigen presenting cell and blocking immune activation via the CD28 and/or CTLA4 pathway; and (b) an immunosuppressive agent in a pharmaceutically acceptable excipient.

24. A method for treating graft versus host disease (GVHD) in a human patient, the method comprising administering to a human patient in need of such treatment a therapeutically effective amount of (a) an anti-B7 monoclonal antibody or an antigen binding fragment thereof, said antibody or fragment thereof binding to a B7 antigen on an antigen presenting cell and blocking immune activation via the CD28 and/or CTLA4 pathway; and (b) an immunosuppressive agent in a pharmaceutically acceptable excipient.

25. A method for treating rheumatoid arthritis in a human patient, the method comprising administering to a human patient in need of such treatment a therapeutically effective amount of (a) an anti-B7 monoclonal antibody or an antigen binding fragment thereof, said antibody or fragment thereof binding to a B7 antigen on an antigen presenting cell and blocking immune activation via the CD28 and/or CTLA4 pathway; and (b) an immunosuppressive agent in a pharmaceutically acceptable excipient.

26. The method of claim 23, wherein said immunosuppressive agent is cyclosporin.

27. The method of claim 24, wherein said immunosuppressive agent is cyclosporin.

28. The method of claim 25, wherein said immunosuppressive agent is cyclosporin.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:

(A) LENGTH: 27 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: Forward Primer for B7, MR67, Figure 2

(xi) SEQUENCE DESCRIPTION: SEQ ID NO:1:

GCGCTGCAGC ATCTGAAGCC ATGGGCC 27

(2) INFORMATION FOR SEQ ID NO:2:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (vi) ORIGINAL SOURCE:
(C) INDIVIDUAL ISOLATE: Backward Primer for B7, MR68

(xi) SEQUENCE DESCRIPTION: SEQ ID NO:2:

CGCGGTACCT TGCTTCTGCG GACACTG 27

(2) INFORMATION FOR SEQ ID NO:3:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: Forward Primer for Soluble B7, MR67

(xi) SEQUENCE DESCRIPTION: SEQ ID NO:3:

GCGCTGCAGC ATCTGAAGCC ATGGGCC 27

(2) INFORMATION FOR SEQ ID NO:4:

(i) SEQUENCE CHARACTERISTICS:
(A) LENGTH: 61 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (vi) ORIGINAL SOURCE:

( C ) INDIVIDUAL ISOLATE: Backward Primer for Soluble B7, MR145

( x i ) SEQUENCE DESCRIPTION: SEQ ID NO:4:

```
GCGCGGTACC TTACTCCATG GGCATGTATT CCTCTTCCTC GTTATCAGGA AAATGCTGTT      60
G                                                                     61
```

( 2 ) INFORMATION FOR SEQ ID NO:5:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: Forward Primer for CD40, MR108

( x i ) SEQUENCE DESCRIPTION: SEQ ID NO:5:

```
GCGTAGATCT GGTCTCACCT CGCCATGGTT CG                                    32
```

( 2 ) INFORMATION FOR SEQ ID NO:6:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
        ( C ) INDIVIDUAL ISOLATE: Backward Primer for CD40, MR112

( x i ) SEQUENCE DESCRIPTION: SEQ ID NO:6:

```
GCGTGGTACC CCACACTCCT GGGTGGGTGC AGCC                                  34
```

( 2 ) INFORMATION FOR SEQ ID NO:7:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: Forward Primer for Soluble CD40, MR108

( x i ) SEQUENCE DESCRIPTION: SEQ ID NO:7:

```
GCGTAGATCT GGTCTCACCT CGCCATGGTT CG                                    32
```

( 2 ) INFORMATION FOR SEQ ID NO:8:

( i ) SEQUENCE CHARACTERISTICS:

```
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
        ( C ) INDIVIDUAL ISOLATE: Backward Primer for Soluble
              CD40, MR150

( x i ) SEQUENCE DESCRIPTION: SEQ ID NO:8:

GCGTGGTACC  TTACTCCATG  GGCATGTATT  CCTCTTCCTC  ATCAGTCTTG  TTTGTGCCTG      60
C                                                                          61
```